(12) United States Patent
Prentiss

(10) Patent No.: US 6,440,100 B1
(45) Date of Patent: Aug. 27, 2002

(54) CONCEALED APPARATUS FOR HANDS FREE BREAST MILK PUMPING AND STORAGE

(76) Inventor: John Gilbert Prentiss, Rte. 1 Box 194, Pamplin, VA (US) 23958

( * ) Notice: Subject to any disclaimer, the term of this patent is extended or adjusted under 35 U.S.C. 154(b) by 279 days.

(21) Appl. No.: 09/583,511

(22) Filed: May 31, 2000

(51) Int. Cl.[7] .................................................. A61M 1/06
(52) U.S. Cl. .............................. 604/74; 604/75; 604/76; 604/326; 604/346
(58) Field of Search ................................ 604/74, 75, 76, 604/73, 315, 320, 322, 323, 326, 118, 119, 346; 119/14.43, 14.47, 14.48, 14.49, 14.51

(56) References Cited

U.S. PATENT DOCUMENTS

| | | | |
|---|---|---|---|
| 22,018 A | 11/1858 | Davidson | |
| 22,080 A | 11/1858 | Lewis | |
| 72,604 A | 12/1867 | Cole | |
| 166,686 A | 8/1875 | Daniels | |
| 603,564 A | * 5/1898 | Hoover | 604/74 |
| 949,414 A | 2/1910 | Cunningham | |
| 3,782,385 A | * 1/1974 | Loyd | 604/74 |
| 4,680,028 A | * 7/1987 | Stuart | 604/74 |
| 5,514,166 A | 5/1996 | Silver et al. | 604/74 |
| 5,575,768 A | 11/1996 | Lockridge et al. | 604/74 |
| 5,616,125 A | 4/1997 | Jelks | 604/74 |
| 5,720,722 A | 2/1998 | Lockridge | 604/74 |
| 5,797,875 A | 8/1998 | Silver | 604/74 |
| 5,810,772 A | 9/1998 | Niederberger | 604/74 |
| 5,954,690 A | 9/1999 | Larsson | 604/74 |
| 6,004,186 A | 12/1999 | Penny | 450/36 |
| 6,004,288 A | * 12/1999 | Hochstedler et al. | 604/74 |
| 6,090,065 A | * 7/2000 | Giles | 604/74 |
| 6,139,521 A | * 10/2000 | Larsson | 604/74 |
| 6,152,896 A | * 11/2000 | Bachman et al. | 604/74 |
| 6,210,360 B1 | * 4/2001 | Kong | 604/73 |
| 6,257,847 B1 | * 7/2001 | Silver et al. | 604/74 |
| 6,270,474 B1 | * 8/2001 | Nuesch | 604/74 |
| 6,273,868 B1 | * 8/2001 | Nordvik | 604/74 |
| 6,287,521 B1 | * 9/2001 | Quay et al. | 604/346 |
| 6,358,226 B1 | * 3/2002 | Ryan | 604/74 |

* cited by examiner

Primary Examiner—Teresa Walberg
Assistant Examiner—Fadi H. Dahbour

(57) ABSTRACT

A concealed apparatus for hands free breast milk pumping and storage includes one or more low profile nipple caps held in place beneath a support brassiere. The system permits concealed, hands free breast pumping in a public environment without any remarkable change in the user's visible appearance. Milk is expressed from the breasts through novel, low profile nipple caps linked to a reservoir via a milk storage conduit. A vacuum is applied to the storage reservoir by any suitable means such as an electric or manual vacuum pump. Suction is thus conveyed through related system components to express milk from the breasts and draw it into the storage reservoir, while being essentially unobserved by others.

20 Claims, 3 Drawing Sheets

CONCEALED APPARATUS FOR HANDS FREE BREAST MILK PUMPING AND STORAGE

FIELD OF INVENTION

The present invention relates to breastmilk pumping and storage systems, more specifically to one which may be used in public, hands free, with elements of the system concealed beneath clothing.

BACKGROUND

Natural breastfeeding is widely accepted as the best way to nurture an infant. However, breastfeeding is not always possible for working mothers and other women who are not able to be present for their babies at every feeding. Because breastmilk is best for babies and breastfeeding requires ongoing practice to sustain optimum lactation, expression of breastmilk with a pump has been a widely accepted practice for many years. Breast pumps range from simple hand operated models that pump one breast at a time to a wide selection of electric models now in use, most of which simultaneously pump both breasts. Currently available breast pumps require exposing the breasts to view, much more than is necessary with breastfeeding. Consequently, mothers who pump usually need a private place in which to express milk. This often presents a serious impediment to breastfeeding and may be a deciding point in a mother choosing not to breastfeed. The most common contemporary breast pumping systems use silicone nipple cups fitted at the top of tubular bottles. One or two bottles are held by the mother in front of her breasts while a hand pump or remote vacuum source expresses milk into the bottles. Examples of this design include Larsson, U.S. Pat. No. 5,954,690 Alternating Suction Breast Pump; Niederberger, U.S. Pat. No. 5,810,772 Mother's Milk Pump; Silver, U.S. Pat. No. 5,797,875, Breast Pump Assembly and Method; and Lockridge, U.S. Pat. No. 5,720,722. These systems all require that the mother hold fairly cumbersome containers in front of her breasts for approximately 15 minutes while pumping, usually necessitating the use of a private room for milk expression. Because many work environments are not set up for mothers to have a private place to pump, these conspicuous systems may be extremely inconvenient, discouraging women from ever starting breastfeeding, or may cause them to eventually discontinue breastfeeding as it may not seem to be worth the trouble of having to express milk in a ladies room. In addition, time away from the work station for pumping may be a problem with unsympathetic employers and busy employees. These systems further are not advantageous while traveling or for use in any public environment.

Good quality breast pumping systems are important to maintaining lactation and long term breastfeeding for many mothers. Breast pumps currently in use make breast pumping a stressful experience for many, reducing milk production and limiting a mother's freedom. Being able to pump in public unnoticed will enable a mother to relax more while pumping and to enjoy greater freedom, thereby enhancing milk supply. The need to hold and manipulate the nipple cups and storage bottles, combined with sometimes stressful pumping environments where a mother may feel rushed, are often responsible for decreased lactation. Consequently, a mother may be forced to resort to full time formula feeding long before she would normally do so.

Hands free pumping affords a mother the ability to simultaneously massage her breasts to enhance milk let down, a procedure that is not possible with most pumps currently in use. To mitigate the disadvantage of holding the storage containers while pumping, several inventions have been patented. These include Penny, U.S. Pat. No. 6,004,186, Apparatus for Securing Suction Devices to a Nursing Mother's Breasts, Lockridge, et. al., U.S. Pat. No. 5,575,768, Device and Kit for Supporting a Breast Shield and Related Pump Equipment; and Silver, et. al., U.S. Pat. No. 5,514,166, Device and Method for Supporting a Breast Shield and Related Pump Equipment. These systems are adaptations of the previously mentioned pumping units, and they leave the somewhat cumbersome storage bottles still suspended in front of the mother's breasts.

A departure from the above systems was patented by Jelks, U.S. Pat. No. 5,616,125. This design places the storage bottles along with pumping gear in a backpack linked to the breasts by tubes. While there are several reasons to question this system's functionality as disclosed, it is noteworthy. It is unclear how the vacuum lines pass through the T-shirt, or how those same lines can enter the apex of the domed nipple cups as specified and be held in place by a T-shirt. They certainly would not remain undetected in public, though no claim is made as to suitability for public use. The lines linking the breasts to the storage bottles are too long to clean easily and would likely need to be discarded after each use. Other drawbacks of Jelk's system include the backpack itself which seems to be cumbersome. Also, milk passes through the pumps before reaching the storage bottles, posing a sanitation and cleaning problem. The system remains unsuitable for anything but covert use, and does not address the principle objects of the present invention.

When $19^{th}$ century women wore corsets covering a majority of the torso, leakage from lactating breasts presented a major problem. To contend with this issue, Daniels, U.S. Pat. No. 166,686 discloses nipple cups to be worn beneath a corset or brassiere with drain lines extending to a remote reservoir. Milk naturally dripping from the breast was thereby prevented from soiling undergarments. More recently, Canadian Patent #2,033,604 was issued to Huynh for an under-bra collection system comprising a low profile nipple cap connected to a collection bottle located below each breast to catch leakage. However, Huynh's design makes no provision for breast pumping and is solely for the expressed purpose of replacing breast pads.

Breast shells were commonly used in the $19^{th}$ century to cope with leaking breasts and were later adapted to conceal public breast feeding in a Victorian society. Davidson, U.S. Pat. No. 22,018, incorporates a breast shell with a tube having a nipple on the end so that an infant can draw milk from the breast while the mother is fully clothed. A similar milk expressing system was patented by Lewis, U.S. Pat. No. 22,080 a week later. The mother could use mouth suction to express small amounts of milk from her breast, then installs a nipple on the same tube and feed her baby from the breast shell. Although these systems may have made breast feeding in public more convenient, they did not provide for expressing and storing quantities milk for later use when the infant and mother could not be in the same location. Expanding on these two designs, Cunningham, U.S. Pat. No. 949,414 added a brassiere, but the system seems nearly impossible to conceal and ill suited for public use.

Also in the $19^{th}$ century, Cole, U.S. Pat. No. 72,604, invented a breast pump having a relatively low profile nipple cup connected to a squeeze bulb via rubber lines. This system was clearly not intended to be worn beneath clothing, as the stated method of operation instructs the user to hold the nipple cup in place while operating the pump "with the other hand". There is no provision for holding the nipple cup in position other than manually, and it is suitable for pumping only one breast at a time. This design is extremely unsanitary since expressed milk had to pass through the squeeze bulb and a long span of latex tubing before reaching the storage vessel. Adequately cleaning these parts would be nearly impossible. Storage means most commonly in use today are 4 ounce tubular polycarbonate bottles, one for each breast in the popular double breasted systems. They are not typically suitable for use as long term storage containers, and expressed milk generally needs to be transferred to other containers for extended freezer storage.

SUMMARY OF INVENTION

The present concealed breastmilk pumping and storage system incorporates elements of the past 150 years in breast milk pumping and storage technology to provide a hybrid system enabling comfortable, concealed use beneath clothing and hands free pumping. The low profile components can be inserted beneath a brassiere or custom support system designed to mask and secure the nipple caps under loose outer clothing. Any suitable vacuum source can be used to develop a negative pressure in the storage reservoir, or the reservoir itself can be designed to be somewhat resilient with a firm shape memory and fitted with an exhaust valve to function as a manual squeeze pump operated by hand. By creating a negative pressure in the storage reservoir from a location normally above the milk level, milk is drawn into the storage reservoir from the breasts without contamination or back flow to the vacuum pump.

Because there is a considerable range in sizes and shapes of women's breast, significant variations on the present theme will be appropriate to provide comfortable, non-obtrusive storage system elements for a wide spectrum of body types. The present pumping system is unobtrusive to the extent that a mother can express breastmilk substantially unobserved while sitting at her desk at the office, traveling in a car, or even while using public transportation.

OBJECTS AND ADVANTAGES

A principle object of the present invention is to enable unobserved breast pumping in a public environment so that a mother can comfortably express milk almost any time, any where, thereby making breastfeeding a more agreeable option for mothers who need to express milk. A second object is to enable hands free breast pumping. A third object is to provide a highly versatile, wearable system that can be used with any suitable vacuum source. A fourth object is to provide a wearable breast milk pumping system that doubles as a collection system for leaking breasts to capture and retain leaked milk. A fifth object is to provide optionally disposable milk storage containers that can be used for freezer storage. A sixth object is to minimize the number of components requiring cleaning in a breast pumping system. A seventh object is to provide a breast pumping system wherein milk flow into or through a remote vacuum pump is substantially eliminated.

DETAILED DESCRIPTION OF THE DRAWINGS

Figure 1:
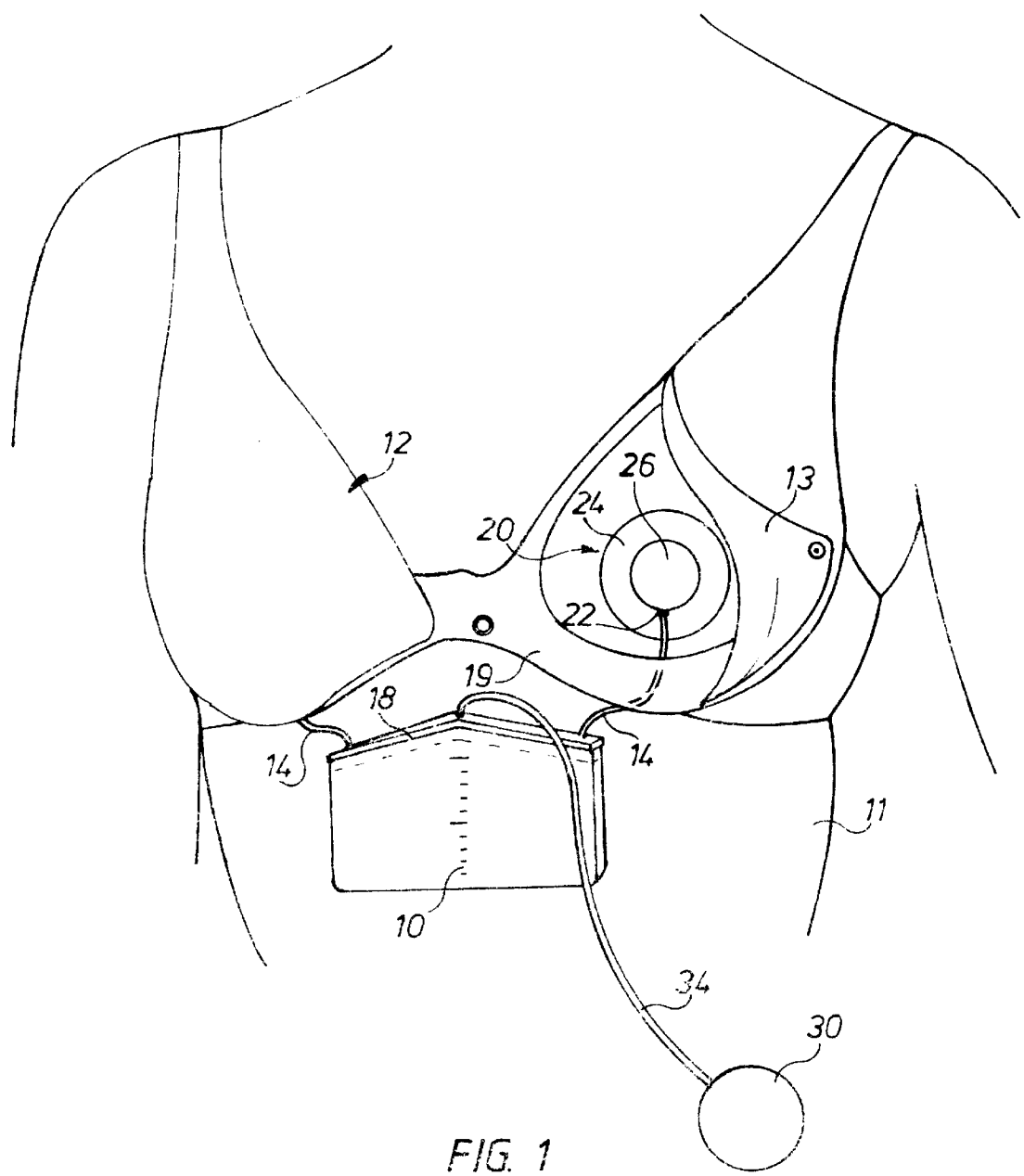
FIG. 1 is a frontal view of the first embodiment of the concealed breast pumping system.

The FIG. 1 depicts the subject invention employing a single low profile reservoir 10 suspended beneath a nursing brassiere 12 with one panel 13 shown open. Reservoir 10 is suspended via milk conduits 14 which are securely, but removably inserted into holes penetrating removable cover 18 which is friction fit into storage vessel 10. Milk conduits 14 pass beneath the lower edge 19 of nursing brassiere 12, and are held between brassiere 12 and body 11 by friction. The system is light weight and will typically be used sitting down, requiring nominal support means for storage vessel 10 which has a capacity of approximately 200 ml. Further support for storage vessel 10 may optionally be added. Milk conduits 14 in this embodiment are approximately 1 mm inside diameter or greater, and extend from removable cover 18 to nipple cap 20, the right side hidden here beneath brassiere 12, typically being identical with the left side. Nipple cap 20 includes annular flange 24 and cavity 26 to sealingly enclose nipple 20, shown in FIG. 4. Nipple cavity 26 must be sufficiently rigid to withstand collapse when a vacuum is applied. Conduit 22 is sized to sealingly receive milk conduit 14. Nipple cap 20 in FIG. 1 is an optionally disposable, vacuum formed thermoplastic unit, detailed in FIG. 2 and FIG. 3. Nipple cap 20 may otherwise be injection molded in a suitable thermoplastic or thermoset elastomer, and may comprise multiple parts as depicted in FIG. 4.

Reservoir 10 may be molded of a resilient material such as a thermoset elastomer having strong shape memory so that the reservoir itself may be used as a squeeze pump when fitted with an exhaust valve. An external vacuum source 30 is used in the figured embodiment, requiring reservoir 10 to be sufficiently rigid to retain its shape when a vacuum is applied via vacuum line 34. In this case, reservoir 10 may be injection molded of a more rigid polymer such as reinforced polypropylene, suitable for freezing and milk storage. Schematic vacuum source 30 may be an electric pump, manual pump or suction means capable of developing a constant or pulsating negative pressure of at least minus 50 mm Hg/in2, these sources being well know to persons versed in the art.

Figure 2:
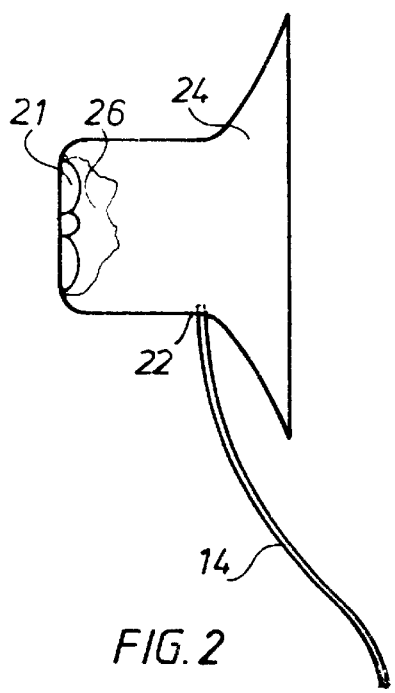
FIG. 2 shows the nipple cap of the FIG. 1 embodiment with a cut-away near the tip.
Figure 3:
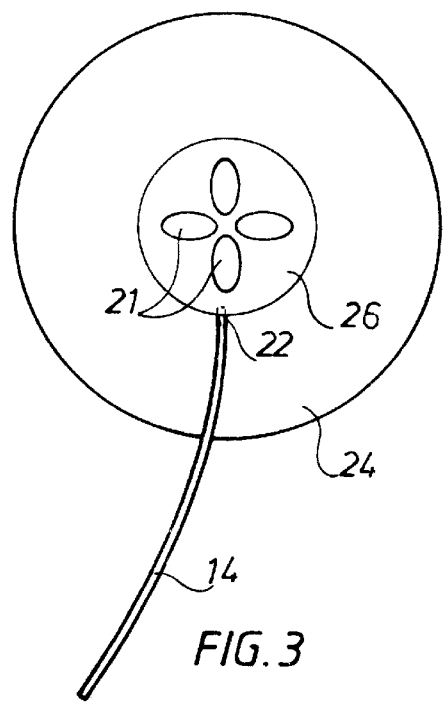
FIG. 3 is a frontal view of the nipple cap of the FIG. 1 and FIG. 2 embodiment.

FIG. 2 is a cut-away of the low profile one piece nipple cap 20 shown in FIG. 1. Nipple cap 20 includes flange 24 and cavity 26 which has ribs 21 at the inner extremity, port 22 and milk conduit 14. FIG. 3 is a frontal view of the nipple cap 20 showing flange 24, cavity 26 with molded ribs 21, port 22, and milk conduit 14.

Figure 4:
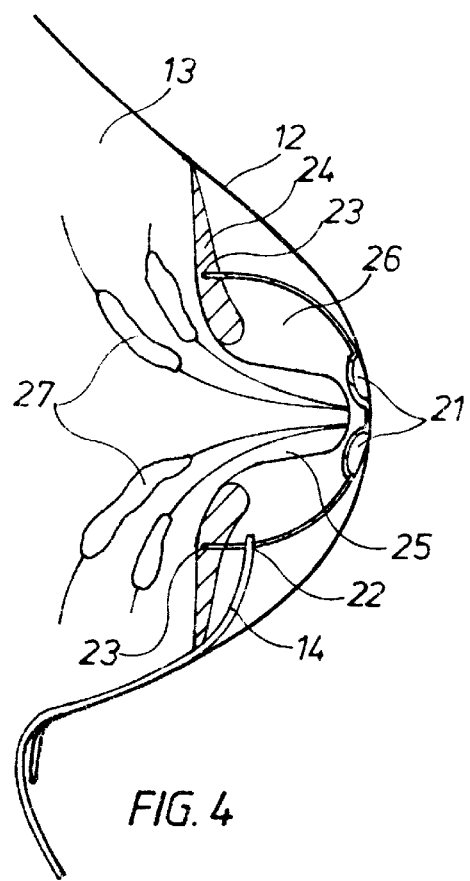
FIG. 4 is a section of a typical breast fitted with a two piece, low profile nipple cap.

FIG. 4 is a section of a typical breast 13 with lactiferous ampulae 27 and nipple 25, fitted with brassiere 12. Two piece nipple cap 20 has resilient flange 24 with annular slot 23 into which rigid, hemispherical cavity 26 is sealingly fitted. Ribs 21 are shown at the inner apex of cavity 26, similar to those shown in FIG. 2 and FIG. 3. Port 22 in cavity 26 is sealingly fitted with milk conduit 14 which leads to reservoir 10 as in FIG. 1.

Figure 5:
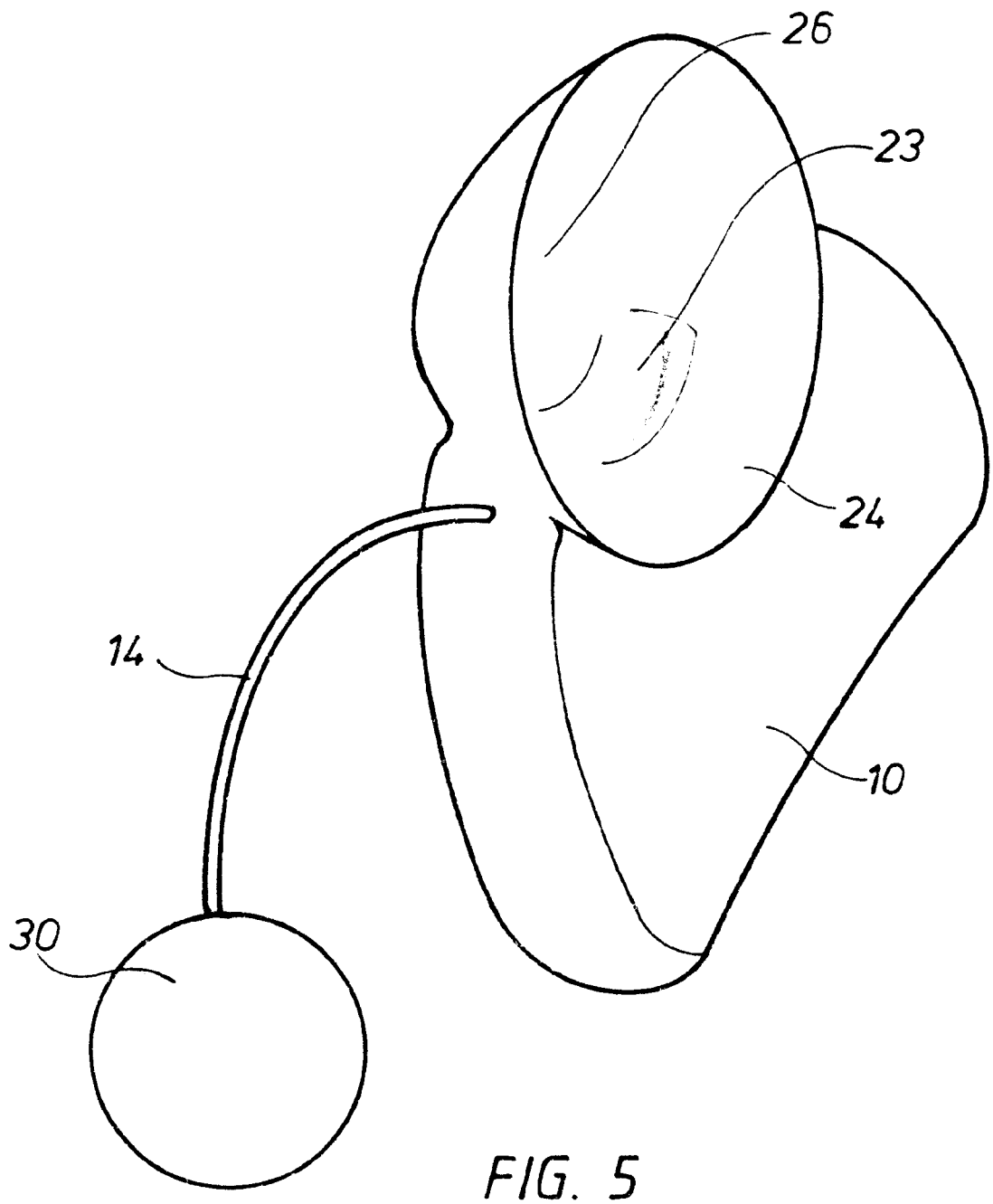
FIG. 5 is a perspective of an abbreviated embodiment of the invention.

The abbreviated embodiment of FIG. 5 shows a one piece, optionally disposable, blow molded unit including a flask-like storage vessel 10, integral flange 24, cavity 26, and vacuum tube 34 connected to schematic vacuum source 30. The milk conduit and port in this case are embodied as a direct transition 23 from cavity 26 to reservoir 10. Reservoir 10 has 100 ml capacity and is sculpted to fit comfortably hidden below the breast.

In operation, vacuum source 30 transmits vacuum via tube 34 into reservoir 10. Suction thence conveys through milk conduit 14 and port 22 to cavity 26. Flange 24 is pressed against the lactiferous sinuses 27 by brassiere 12. A seal is simultaneously created around flange 24, preventing air from entering cavity 26 from around flange 24. Optional ribs 21 prevent milk flow from inadvertently being blocked when nipple 25 is drawn by vacuum against the inner wall of cavity 26. The vacuum thus transmitted to cavity 26 withdraws milk through nipple 25, port 22 and milk conduit 14, thence into reservoir 10. Applying a pulsating or continuous vacuum to the system imitates a suckling infant, thus expressing milk from the breasts to the reservoir for later use. Unlike any system known to the inventor, the concealed components can be worn in a public environment.

RAMIFICATIONS AND SCOPE

Numerous alternatives to the figured embodiments exist for the construction of the subject breastmilk pumping and storage system. Due to variations in human form, size and configuration of the hidden components may vary of necessity. Materials and method of manufacture may also vary widely while remaining within the spirit of the invention, as components may be both disposable or non disposable, flexible and rigid, one piece or multiple piece, or reinforced units having external or internal ribs. A liner bag may be used with the rigid storage reservoir for later milk storage. Figure enhancing brassieres may be used to support the elements of the system. Any vacuum means including all suitable manual and electric pumps or mouth suction can be applied to create a vacuum.

Those skilled in the art will appreciate that the concepts disclosed herein may readily inspire other concealed embodiments fulfilling the objectives of the present invention. It is therefore intended that the claims be regarded as including such equivalent constructions insofar as they do not depart from the spirit and scope of the present invention. The appended drawings depict preferred embodiments without intending to limit the scope of the invention which is more fully delineated by the claims that follow.

I claim:

1. A breast milk pumping and storage system for expressing and collecting human milk, the improvements comprising concealed components wherein at least one nipple cap presents a low external profile to permit hidden use beneath loose outer garments, said breast milk pumping and storage system including support means to press said nipple cap sealingly against said breast so as to be substantially concealed beneath said loose outer garments, said nipple cap comprising a hollow cavity having outside and inside surfaces to surround and enclose a nipple drawn out by vacuum without blocking flow from milk ducts at the tip of said nipple, said hollow cavity further including: a.) an annular opening through which said nipple is received, b.) a substantially conical flange portion coaxial with said annular opening, said flange portion serving to cushion said breast while stimulating the lactiferous ampulae beneath the areola of said breast and providing a vacuum seal between said breast and said annular opening, and c.) a milk delivery conduit communicating between said hollow cavity and a milk storage reservoir, said conduit being so disposed as to be substantially concealed when covered by said loose outer garments, said breast milk pumping and storage system further including means to develop a negative pressure of at least minus 50 mm Hg/in2 within said milk storage reservoir, said milk delivery conduit and said hollow cavity.

2. The breast milk pumping and storage system of claim 1 wherein both said breasts are pumped simultaneously.

3. The breast milk pumping and storage system of claim 1 wherein said milk delivery conduit comprises non-collapsible tubing having an inside diameter of approximately 1 mm.

4. The breast milk pumping and storage system of claim 1 wherein said hollow cavity includes at least one rib to facilitate milk flow from said nipple to said milk delivery conduit.

5. The breast milk pumping and storage system of claim 1 wherein said vacuum producing means is selected from a list including an electric vacuum pump, a hand operated vacuum pump, an arm operated vacuum pump, a leg operated vacuum pump, a squeeze bulb pump, a squeezable resilient reservoir with an exhaust valve, a foot operated vacuum pump, a concealed vacuum pump, a non-concealed vacuum pump, a remote vacuum pump, and mouth suction.

6. The breast milk pumping and storage system of claim 1 wherein an independent vacuum pump is used for each breast.

7. The breast milk pumping and storage system of claim 1 wherein said storage reservoir is a singular container suspended substantially beneath and between the breasts.

8. The breast milk pumping and storage system of claim 1 wherein said non-collapsible conduit means is neoprene tubing.

9. The breast milk pumping and storage system of claim 1 wherein said non-collapsible conduit means is disposable.

10. The breast milk pumping and storage system of claim 1 wherein said storage reservoir includes a liner bag for storing milk.

11. The breast milk pumping and storage system of claim 1 wherein said storage reservoir may be employed as a storage container.

12. The breast milk pumping and storage system of claim 1 wherein said means to press said nipple cap sealingly against said breast is a brassiere.

13. The breast milk pumping and storage system of claim 1 wherein said hollow cavity in said nipple cap is integral with said milk storage reservoir.

14. The breast milk pumping and storage system of claim 1 wherein said milk delivery conduit is integral with said milk storage reservoir.

15. The breast milk pumping and storage system of claim 1 wherein said reservoir is not concealed.

16. An annular nipple cap to cover the fore portion of a human female breast, said nipple cap comprising a hollow cavity having outside and inside surfaces to surround and enclose a nipple, providing room within said hollow cavity to permit said nipple to be distended by vacuum without blocking flow from milk ducts at the tip of said nipple, said hollow cavity further including: a.) an annular opening through which said nipple is received, b.) a substantially conical flange portion coaxial with said annular opening, said flange portion serving to cushion said breast while stimulating the lactiferous ampulae beneath the areola of said breast and providing a vacuum seal between said breast and said annular opening and c.) a milk delivery conduit communicating between said hollow cavity and a breastmilk pumping system, said conduit being so disposed as to be substantially concealed when covered by a loose outer garments.

17. The nipple cap of claim 16 wherein said nipple cap is a molded polymer.

18. The nipple cap of claim 16 wherein said nipple cap comprises multiple molded parts.

19. The nipple cap of claim 16 wherein said nipple cap is integral with said milk storage reservoir.

20. The nipple cap of claim 16 wherein said flange portion is an independent, molded resilient member removably attached to said hollow cavity.

* * * * *